US006809117B2

(12) United States Patent
Enikolopov et al.

(10) Patent No.: US 6,809,117 B2
(45) Date of Patent: Oct. 26, 2004

(54) THERAPEUTIC USES OF NITRIC OXIDE INHIBITORS

(75) Inventors: Grigori N. Enikolopov, Cold Spring Harbor, NY (US); Natalia I. Peunova, Cold Spring Harbor, NY (US); Boris A. Kuzin, Moscow (RU); Hollis Cline, Cold Spring Harbor, NY (US); Tatiyana Michurina, Moscow (RU)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 8 days.

(21) Appl. No.: 10/288,639

(22) Filed: Nov. 4, 2002

(65) Prior Publication Data

US 2003/0119905 A1 Jun. 26, 2003

Related U.S. Application Data

(63) Continuation of application No. 09/384,318, filed on Aug. 27, 1999, now abandoned, which is a continuation of application No. 08/969,475, filed on Nov. 13, 1997, now Pat. No. 5,977,181.
(60) Provisional application No. 60/045,411, filed on May 2, 1999, and provisional application No. 60/030,690, filed on Nov. 13, 1996.

(51) Int. Cl.[7] .................. A61K 3/19; A61K 31/557; A61K 31/155

(52) U.S. Cl. .............. 514/565; 514/631; 514/632; 514/665; 514/563

(58) Field of Search ................ 514/631, 632, 514/665, 561, 565, 653

(56) References Cited

FOREIGN PATENT DOCUMENTS

| WO | WO 94/28013 | 12/1994 |
|---|---|---|
| WO | WO 98/20865 | 5/1998 |

OTHER PUBLICATIONS

Benrath, J., et al., Substance P and nitric oxide mediate wound healing of ultraviolet photodamaged rat skin: evidence for an effect of nitric oxide on keratinocyte proliferation, *Neurosci. Let., 200*:17–20 (1995).
Bidri, M., et al., "Involvement of Cyclic Nucleotides in the Immunomodulatory Effects of Nitric Oxide on Murine Mast Cells" *Biochem. Biophys. Res. Comm., 210*:507–517 (1995).
Blottner, D., et al., "Histochemistry of Nitric Oxide Synthase in the Nervous System," *Histochem. Journal, 27*:785–811 (1995).
Bonham, C.A., et al., "Nitric Oxide Production by Mouse Bone Marrow–Derived Dendritic Cells," *Transplantation, 62*:1871–1877 (1996).
Brandi, M.L., et al., "Bidirectional Regulation of Osteoclast Function by Nitric Oxide Synthase Isoforms," *Proc. Natl. Acad. Sci. USA, 92*:2954–2958 (1995).

Bredt, D.S. and Snyder, S.H., "Nitric Oxide: A Physiologic Messenger Molecule," *Annu. .Rev. Biochem., 63*:175–195 (1994).
Bredt, D.S. and Snyder, S.H., "Transient Nitric Oxide Synthase Neurons in Embryonic Cerebral Cortical Plate, Sensory Ganglia, and Olfactory Epithelium," *Neuron, 13*:301–313 (1994).
Clemens, W., et al., "Inducible Production of Nitric Oxide in Osteoblast–Like Cells and in Fetal Mouse Bone Explants is Associated with Suppression of Osteoclastic Bone Resorption," *J. Clin. Invest., 93*:1465–1472 (1994).
Collin–Osdoby, P., et al., "Bone Cell Function, Regulation, and Communication: A Role for Nitric Oxide," *J. Cellular Biochem., 57*:399–408 (1995).
Cramer, K.S., et al., "Transient Expression of NADPH–Diaphorase in the Lateral Geniculate Nucleus of the Ferret During Early Postnatal Development," *J. of Comparative Neurology, 353*:306–316 (1995).
Decker, K.F. and Obolenskaya, M.Y., "Cytokines, Nitric Oxide Synthesis and Liver Regeneration," *J. Gastroenterology and Hepatology, 10*:S12–S17 (1995).
Drobyski, W.R., et al., "Inhibition of Nitric Oxide Production is Associated with Enhanced Weight Loss, Decreased Survival, and Impaired Alloengraftment in Mice Undergoing Graft–Versus–Host Disease After Bone Marrow Transplantation," *Blood, 84*:2363–2373 (1994).
Dugas, B., et al., "Nitric Oxide, a Vital Poison Inside the Immune and Inflammatory Network," *63rd Forum in Immunology*, pp. 664–670 (1995).
Firkin, F.C., et al., "Differential action of diffusible molecules in long–term marrow culture on proliferation of leukaemic and normal haemopoietic cells," *Br. J. Haematol., 84*:8–15 (1993).

(List continued on next page.)

*Primary Examiner*—Theodore J. Criares
(74) *Attorney, Agent, or Firm*—Fish & Neave; James F. Haley, Jr.; Z. Ying Li

(57) ABSTRACT

The present invention is based on the discovery that nitric oxide (NO) is an important growth regulator in an intact developing organism. In particular, the present invention relates to a method of increasing in a mammal a population of hematopoietic stem cells in bone marrow which are capable of undergoing normal hematopoiesis and differentiation, wherein the bone marrow is contacted with an inhibitor of NO, such as an inhibitor of nitric oxide synthase (NOS), thereby producing bone marrow having an increased population of hematopoietic stem cells which are capable of undergoing normal hematopoiesis and differentiation. The present invention also relates to a method of increasing a population of cells in S phase in a tissue of a mammal, comprising contacting the tissue with an inhibitor of NO, such as an inhibitor of NOS. The invention also pertains to a method of regenerating tissue in an adult mammal comprising contacting a selected tissue (e.g., blood, skin, bone and digestive epithelium), or precursor cells of the selected tissue, with an inhibitor of NO, thereby inhibiting differentiation and inducing proliferation of cells of the tissue.

11 Claims, No Drawings

OTHER PUBLICATIONS

Forstermann, U., et al., "Expression and Expressional Control of Nitric Oxide Synthases in Various Cell Types," *Adv. Pharmacol., 34*:171–186 (1995).

Gally, J.A., et al., "The NO Hypothesis: Possible Effects of a Short –Lived, rapidly Diffusible Signal in the Development and Function of the Nervous System," *Proc. Natl. Acad. Sci. USA, 87*:3547–3551 (1990).

Gansauge, S., et al., "Exogenous, but not Endogenous, Nitric Oxide increases proliferation rates in senescent human fibroblasts," *FEBS Left (Netherlands), 410*:160–164 (1997).

Garg, U.C. and Hassid, A., "Inhibition of Rat Mesangial Cell Mitogenesis By Nitric Oxide–Generating Vasodilators", *Amer. Phys. Soc., 257*:F60–F66 (1989).

Garthwaite, J. and Boulton, C.L., "Nitric Oxide Signaling in the Central Nervous System," *Annu. Rev. Physiol., 57*:683–706 (1995).

Gilad, V.H., et al., "Accelerated recovery following polyamines and aminoguanidine treatment after facial nerve injury in rats," *Brain Res., 724*:141–144 (1996).

Guo, J., et al., "Endothelial Preserving Actions of a Nitric Oxide Donor in Carotid Arterial Intimal Injury," *Meth. Find. Exp. Clin. Pharmacol., 16*:347–354 (1994).

Hoffman, R.A., et al., "Attenuation of Lethal Graft–Versus–Host Disease by Inhibition of Nitric Oxide Synthase," *Transplantation, 63*:94–100 (1997).

Hoffman, R.A., et al., "Bystander Injury of Host–Lymphoid Tissue During Murine Graft–Versus–Host Disease is Mediated by Nitric Oxide," *Transplantation, 61*:610–618 (1996).

Holliday, L.S., et al., "Low NO concentrations inhibit osteoclast formation in mouse marrow cultures by cGMP—dependent mechanism," *Am. J. Physiol., 272*:F283–F291 (1997).

Hortelano, S., et al., "Nitric Oxide is Released in Regenerating Liver After Partial Hepatectomy," *21*:776–786 (1995).

Jun, C., et al., "High–dose nitric oxide induces apoptosis in HL–60 human myeloid leukemia cells," *Exp. Mol. Med., 28*:101–108 (1996).

Kaplan, J.M., et al., "Inhibition of Lymphoproliferative Responses by Sk&F 105685, A Novel Anti–Arthritic Agent," *J. Clin. Lab. Immunol., 36*:49–58 (1991).

Knox, L.K., et al., "Nitric Oxide Synthase Inhibitors Improve Skin Flap Survival in the Rat," *Microsurgery, 15*:708–711 (1994).

Krenger, W. et al., "Interferonγ Suppresses T–Cell Proliferation to Mitogen Via the Nitric Oxide Pathway During Experimental Acute Graft–Versus–Host Disease," *Blood, 88*:1113–1121 (1996).

Kuzin, B., et al., "Nitric Oxide Regulates Cell Proliferation during Drosophila Development," *Cell, 87*:639–649 (1996).

Kwon, N.S., et al., "Inhibition of Tumor Cell Ribonucleotide Reductase by Macrophage–derived Nitric Oxide", *J. Exp. Med, 174*:761–767 (1991).

Laskin, D., et al. "Role of Nitric Oxide in Hematosuppression and Benzene–induced Toxicity," *Environ. Health Perspect., 104*:1283–1287 (1996).

Laskin, J. et al., "Distinct actions of benzene and its metabolites on nitric oxide production by bone marrow leukocytes," *J. Leukocyte Biol., 57*:422–426 (1995).

Lee, Y. et al., "Changes of Nitric Oxide Synthase Activity and Free Methylarginines Contents in Regenerating Rat Liver After Partial Hepatectomy," *Arch. Pharm. Res., 20*:239–246 (1997).

Lepoivre, M., et al., "Antiproliferative effects of NO synthase products," *Res. Immunol., 142*:580–583 (1991).

Lu, L., et al., "Induction of Nitric Oxide Synthase in Mouse Dendritic Cells by IFN–Y, Endotoxin, and Interaction with Allogeneic T Cells," *J. Immunol., 157*:3577–3586 (1996).

Maciejewski, J.P., et al., "Nitric Oxide Suppression of Human Hematopoiesis In Vitro," *J. Clin. Invest., 96*(2):1085–1092 (1995).

Magrinat, G., et al., "Nitric Oxide Modulation of Human Leukemia Cell Differentiation and Gene Expression," *Blood, 80*:1880–1884 (1992).

Muñoz–Fernández, M.A., et al., "Tumor Necrosis Factor–α (TNF–α), Interferon–γ, and Interleukin–6 but Not TNF–β Induce Differentiation of Neuroblastoma Cells: The Role of Nitric Oxide," *J. Neurochem., 62*:1330–1336 (1994).

Ogden, J.E. and Moore, P.K., "Inhibition of nitric oxide synthase–potential for a novel class of therapeutic agent?," *Trends Biotechnol, 13*:70–78 (1995).

Ouaaz, F., "Nitric Oxide in Human Haematopoiesis, "*Res. Immunol., 146*:678–681 (1995).

Park, S., et al., "Stem Cell Factor Protects Bone Marrow–Derived Cultured Mast Cells (BMCMC) From Cytocidal Effect of Nitric Oxide Secreted by Fibroblasts in Murine BMCMC–Fibroblasts Coculture," *Biochem. Mol. Biol. Int., 40*:721–729 (1996).

Pascual, D.W., et al., "Nitric Oxide Mediates Immune Dysfunction in the Spontaneously Hypertensive Rat," *Hypertension, 21*:185–194 (1993).

Peunova, N., et al., "Nitric oxide triggers a switch to growth arrest during differentiation of neuronal cells," *Nature, 375*:68–73 (1995).

Punjabi, C., et al., "Role of Nitric Oxide in the Regulation of Bone Marrow Cell Proliferation," *J. Leukocyte Biol.,* no. Suppl 3, 1992, p. 31 (1992).

Punjabi, C.J., et al., "Enhanced Production of Nitric Oxide by Bone Marrow Cells and Increased Sensitivity to Macrophage Colony–Stimulating Factor (CSF) and Granulocyte–Macrophage CSF After Benzene Treatment of Mice," *Blood, 83*:3255–3263 (1994).

Punjabi, C.J., et al., "Production of Nitric Oxide by Murine Bone Marrow Cells," *J. Immunol., 149*:2179–2184 (1992).

Raul, F., et al., "Beneficial Effects of L–Arginine on Intestinal Epithelial Ischemic Damage in Rats," *Digestion, 56*:400–405 (1995).

Roskams, A.J., et al., "Nitric Oxide Mediates the Formation of Synaptic Connections in Developing and Regenerating Olfactory Receptor Neurons," *Neuron, 13*:289–299 (1994).

Schobersberger, W., et al., "Nitric oxide donors suppress erythropoietin production in vitro," *Pflügers Arch. Eur. J. Physiol., 432*:980–985 (1996).

Shaul, P.S., "Nitric Oxide in the Developing Lung," *Advances in Pediatrics, 42*:367–414 (1995).

Tsukahara, H., et al., "Effect of Nitric Oxide Synthase Inhibitors on Bone Metabolism in Growing Rats," *Am. J. Physiol. 270 (Endocrinol. Metab. 33)*:E840–E845 (1996).

Vilpo, J.A., et al., "Mode of Cytoztatic action of mesoionic oxatriazole nitric oxide donors in proliferating human hematopoietic cells," *Anti–Cancer Drug Design, 12*:75–89 (1997).

Wetts, R., et al., "Transient and Continuous Expression of NADPH Diaphorase in Different Neuronal Populations of Developing Rat Spinal Cord," *Developmental Dynamics, 202*:215–228 (1995).

Young, R., et al., "Suppression of T Cell Proliferation by Tumor–Induced Granulocyte–Macrophage Progenitor Cells Producing Transforming Growth Factor–β and Nitric Oxide," *J. Immunol., 156*:1916–1922 (1996).

Zochodne, D.W., et al., "Inhibition of nitric oxide synthase enhances peripheral nerve regeneration in mice," *Neurosci. Let., 228*:71–74 (1997).

Zwadlo–Klarwasser, G., et al., "Inhibition of Spontaneous and Mitogen–Induced Lymphocyte Proliferation by Murine Bone Marrow–Derived Macrophages: Role of Prostaglandins, Nitric Oxides and Cell–to–Cell Contact," *Scand. J. Immunol., 40*:10–15 (1994).

THERAPEUTIC USES OF NITRIC OXIDE INHIBITORS

RELATED APPLICATIONS

This application is a continuation of U.S. application Ser. No. 09/384,318, filed Aug. 27, 1999, now abandoned which is a continuation of U.S. application Ser. No. 08/969,475, filed Nov. 13, 1997, now U.S. Pat. No. 5,977,181, which claims the benefit of U.S. Provisional application Ser. No. 60/030,690, filed Nov. 13, 1996, and benefit of U.S. Provisional application Serial No. 60/045,411, filed May 2, 1997. The teachings of these prior applications are incorporated herein in their entirety.

GOVERNMENT SUPPORT

Work described herein was supported by Grant No. 5RO1NS32764 from the National Institutes of Health. The United States Government has certain rights in the invention.

BACKGROUND OF THE INVENTION

Organ development requires a tightly controlled program of cell proliferation followed by growth arrest and differentiation and, often, programmed cell death. The balance between the number of cell divisions and the extent of subsequent programmed cell death determines the final size of an organ (reviewed by Bryant and Simpson, Quart. *Rev. of Biol.* 59:387–415 (1984); Raft, *Nature* 356:397–400 (1992)). Although much of the cellular machinery that determines the timing of onset and cessation of cell division per se is well understood (reviewed by Hunter and Pines, *Cell* 79:573–582 (1994); Morgan, *Nature* 374:131–134 (1995); Weinberg, *Cell* 81:323–330 (1995)), little is known about the signals that cause discrete groups of cells and organs to terminate growth at the appropriate cell number and size. A better understanding of the signals involved provides possible targets for manipulating the cellular machinery resulting in therapeutic benefits for a number of conditions.

SUMMARY OF THE INVENTION

The present invention is based on the discovery that nitric oxide (NO) is an important growth regulator in an intact developing organism. In particular, the present invention relates to a method of increasing in a mammal a population of hematopoietic stem cells, including precursors to myeloid, lymphoid and erythroid cells, in bone marrow which are capable of undergoing normal hematopoiesis and differentiation, wherein the bone marrow is contacted with an inhibitor of NO, such as an inhibitor of nitric oxide synthase (NOS), thereby producing bone marrow having an increased population of hematopoietic stem cells which are capable of undergoing normal hematopoiesis and differentiation. The method can be carried out in vivo or ex vivo. In addition, the method can be used to prevent differentiation of erythroid cells and/or myeloid cells in the mammal. The method can further comprise contacting the bone marrow with at least one agent (e.g., a hematopoietic growth factor) which induces differentiation of a selected hematopoietic stem cell population.

The present invention also relates to a method for treating a mammal to increase a population of hematopoietic stem cells in bone marrow of the mammal which are capable of undergoing normal hematopoiesis and differentiation. In the method, the bone marrow of the mammal is contacted with an inhibitor of NOS, thereby producing bone marrow having an increased population of hematopoietic stem cells which are capable of undergoing normal hematopoiesis and differentiation. The method can further comprise contacting the bone marrow with at least one agent which induces differentiation of a selected hematopoietic stem cell population.

In one embodiment of the method for treating a mammal to increase a population of hematopoietic stem cells in bone marrow of the mammal which are capable of undergoing normal hematopoiesis and differentiation, bone marroow which is to be transplanted is obtained, wherein the bone marrow to be transplanted can be obtained from the mammal being treated (autologous transplantation) or from another mammal (heterologous transplantation). The bone marrow to be transplanted is contacted with an inhibitor of NOS. The bone marrow which is to be transplanted is transplanted into the mammal being treated, thereby providing the mammal with bone marrow having an increased population of hematopoietic stem cells which are capable of undergoing normal hematopoiesis and differentiation. The method can further comprise treating the mammal with an inhibitor of NOS before or after transplanting the bone marrow. Alternatively, the method can further comprise treating the mammal with an enhancer of NOS before or after transplanting the bone marrow.

The present invention also relates to a method of increasing a population of dividing cells in a tissue of a mammal comprising contacting the cells with an inhibitor of nitric oxide. In one embodiment, the present invention also relates to a method of increasing a population of cells in S phase in a tissue of a mammal, comprising contacting the tissue with an inhibitor of NO, such as an inhibitor of NOS. In one embodiment, the method results in an increase in the size of an organ in which the tissue is occurs. Furthermore, as described herein the cells in S phase can be used in gene therapy.

The present invention also relates to a method of decreasing a population of cells in S phase in a tissue of a mammal and inducing differentiation of the cells, comprising contacting the tissue with an enhancer of NO, such as an enhancer of NOS. In one embodiment, the method results in a decrease in the size of an organ with which the tissue is associated.

The present invention also relates to a method of coordinating developmental decisions of a cell type in a mammal, comprising introducing NO into the cell type or a precursor of the cell type, thereby inhibiting proliferation of the cell type or a precursor of the cell type and inducing differentiation of the cell type or a precursor of the cell type.

A method of inducing differentiation in a mammalian cell population comprising contacting the cell population with NO or a NO enhancer is also encompassed by the present invention.

The invention also pertains to a method of regenerating tissue in an adult mammal comprising contacting a selected tissue (e.g., blood, skin, bone and digestive epithelium), or precursor cells of the selected tissue, with an inhibitor of NO, thereby inhibiting differentiation and inducing proliferation of cells of the tissue, then contacting the selected tissue with a compound (e.g., nitric oxide, a growth factor or a combination of both) which inhibits proliferation and induced differentiation. In one embodiment, the method involves repopulating an organ or tissue (e.g., muscle or nerve fiber) comprised of normally nondividing cells by contacting a selected organ or tissue, or precursor cells of the selected organ or tissue, with an inhibitor of NO, thereby inhibiting differentiation and inducing proliferation of cells of the organ or tissue, then contacting the selected organ or tissue with a compound which inhibits proliferation and induced differentiation.

The invention also encompasses a method of producing a subpopulation of hematopoietic cells. In the method, bone marrow is contacted with an inhibitor of NOS, thereby producing bone marrow having an increased population of hematopoietic stem cells which are capable of undergoing normal hematopoiesis and differentiation; and at least one agent (e.g., a hematopoietic growth factor) selected to induce specific differentiation of the hematopoietic stem cell population, thereby producing a subpopulation of hematopoietic cells.

Identification of NO as an important growth regulator in an organism provides for various therapeutic applications in humans and other mammals.

DETAILED DESCRIPTION OF THE INVENTION

Results of the work described herein have shown that a transcellular messenger (nitric oxide (NO)) plays a critical role in tissue differentiation and organism development. NO regulates the balance between cell proliferation and cell differentiation in the intact developing organism. Increased production of NO permits cessation of cell division and subsequent differentiation of cell in a tissue, whereas removal of the NO-mediated growth arrest promotes cell division.

Accordingly, the present invention relates to a method of increasing in a mammal a population of hematopoietic stem cells, including precursors to myeloid, lymphoid and erythroid cells, in bone marrow which are capable of undergoing normal hematopoiesis and differentiation, by contacting the bone marrow with an inhibitor of NO, such as an inhibitor of NOS. The present invention includes a method for treating a mammal to increase a population of hematopoietic stem cells in bone marrow of the mammal which are capable of undergoing normal hematopoiesis and differentiation, in which the bone marrow of the mammal is contacted with an inhibitor of NOS.

The present invention also relates to a method of increasing a population of dividing cells in a tissue of a mammal comprising contacting the cells with an inhibitor of nitric oxide. In one embodiment, the present invention can also be used to increase a population of cells (targeted cells) in S phase in a tissue of a mammal relative to a similar tissue in an untreated mammal, by contacting the tissue with an inhibitor of NO, such as an inhibitor of NOS. In one embodiment, the method results in an increase in the size of an organ with which the tissue is associated. Conversely, the present invention can also be used to decrease a population of cells in S phase in a tissue of a mammal and inducing differentiation of the cells, comprising contacting the tissue with an enhancer of NO, such as an enhancer of NOS. In one embodiment, the method results in a decrease in the size of an organ with which the tissue is associated. Furthermore, as described herein the cells in S phase can be used in gene therapy.

The present invention also relates to a method of coordinating developmental decisions of a cell type in a mammal, comprising introducing NO into the cell type or a precursor of the cell type, thereby inhibiting proliferation of the cell type or a precursor of the cell type and inducing differentiation of the cell type or a precursor of the cell type. A method of inducing differentiation in a mammalian cell population comprising contacting the cell population with NO or a NO enhancer is also encompassed by the present invention.

The invention also pertains to a method of regenerating tissue in an adult mammal. The method comprises contacting a selected tissue with an inhibitor of NO, thereby inhibiting differentiation and inducing proliferation of cells of the tissue, then contacting the selected tissue with a compound which inhibits proliferation and induces differentiation of the proliferated cells to cells characteristic of the tissue. In one embodiment, the method involves repopulating an organ or tissue (e.g., muscle or nerve fiber) having normally nondividing cells comprising contacting a selected organ or tissue with an inhibitor of NO, thereby inhibiting differentiation and inducing proliferation of cells of the organ or tissue, then contacting the selected organ or tissue with a compound which inhibits proliferation and induces differentiation of the proliferated cells to cells characteristic of the organ or tissue. Compounds which inhibit proliferation and induce differentiation include NO, an enhancer of NO, a growth factor. One or more these compounds can be used to inhibit proliferation and induce differentiation.

Tissue which can be regenerated using the methods described herein include blood, skin, bone and digestive epithelium, nerve fiber, muscle, cartilage, fat or adipose tissue, bone marrow stroma and tendons.

The methods described herein can further comprise the step of contacting the target cells (e.g., bone marrow) with at least one agent which induces differentiation of a selected hematopoietic stem cell population to a particular cell type (e.g., erythrocytes, macrophages, lymphocytes, neutrophils and platelets). For example, in the embodiment wherein a mammal is treated to increase a population of hematopoietic stem cells in the bone marrow of the mammal by contacting the bone marrow of the mammal with an inhibitor of NOS, the increased population of bone marrow cells can be contacted with an agent, such as a hematopoietic growth factor, which will cause or promote differentiation of the cells of a particular cell type. Agents, such as hemopoietic growth factors, which can be used in the methods of the present invention to induce differentiation of the increased or expanded number of cells produced by contacting cells with a NOS inhibitor include, for example, erythropoietin, G-CSF, GM-CSF and interleukins such as IL-1, IL-2, IL-3 and IL-6. Alternatively, the methods described herein can further comprise the step of contacting the bone marrow with at least one agent which further induces or maintains proliferation of the selected hematopoietic stem cell population to a particular cell type (e.g., erythrocytes, macrophages, lymphocytes, neutrophils and platelets).

Inhibitors of NO for use in the present invention include, for example, NO scavengers such as 2-phenyl-4,4,5,5-tetraethylimidazoline-1-oxyl-3-oxide (PTIO), 2-(4-carboxyphenyl)-4,4,5,5-tetraethylimidazoline-1-oxyl-3-oxide (Carboxy-PTIO) and N-methyl-D-glucamine dithiocarbamate (MGD); and NOS inhibitors such as N-nitro-L-arginine methyl ester (L-NAME), N-monomethyl-L-arginine (L-NMMA), 2-ethyl-2-thiopseudourea (ETU), 2-methylisothiourea (SMT), 7-nitroindazole, aminoguanidine hemisulfate and diphenyleneiodonium (DPI).

Enhancers of NO include, for example, NOS enhancers, and NO donors such as sodium nitroprusside (SNP), S-nitroso-N-acetylpenicillamine (SNAP), S-nitrosoglutathione (SNOG, GSNO), diethylamine NONOate (DEA/NO), DETA/NO (NOC-18), 3-morpholinosydnonimine (SIN-1) and spermine NONOate (Sper/NO).

NO is a diffusible multifunctional second messenger that has been implicated in numerous physiological functions in mammals, ranging from dilation of blood vessels to immune response and potentiation of synaptic transmission (Bredt and Snyder, *Annu. Rev. Biochem* 63:175–195 (1994); Nathan and Xie, *Cell* 78:915–918 (1994); Garthwaite and Boulton, *Annu. Rev. Physiol.* 57:683–706 (1995)). NO is produced from arginine by NOS in almost all cell types. A group of three chromosomal genes, giving rise to numerous isoforms of NOS, have been cloned from mammalian cells (Knowles and Moncada, *Biochem. J.* 298:249–259 (1994); Wang and Marsden, *Adv. Pharmacol.* 34:71–90 (1995)), and recently a Drosophila NOS gene, whose coding structure resembles the gene for the mammalian neuronal isoform, has been isolated (Regulski and Tully, *Proc. Natl. Acad. Sci. USA* 92:9072–9076 (1995)).

Cell division and subsequent programmed cell death in imaginal discs of Drosophila larvae determine the final size of organs and structures of the adult fly. Results described herein show that NO is involved in controlling the size of body structures during Drosophila development. These results demonstrate that NOS is expressed at high levels in developing imaginal discs. Inhibition of NOS in larvae causes hypertrophy of organs and their segments in adult flies, whereas ectopic expression of NOS in larvae has the opposite effect. Blocking apoptosis in eye imaginal discs unmasks surplus cell proliferation and results in an increase in the number of ommatidia and component cells of individual ommatidia. These results demonstrate the activity of NO as an antiproliferative agent during Drosophila development, controlling the balance between cell proliferation and cell differentiation. Moreover, results shown here demonstrate that NO acts as a crucial regulator of hematopoiesis after bone marrow (BM) transplantation. NO regulates the maturation of both the erythroid and myeloid lineages. These data demonstrate that manipulations of NOS activity and NO levels during hematopoiesis can be used to alter (enhance or reduce) blood cell production. This is useful for preventive and therapeutic intervention.

During Drosophila development, the structure, size, and shape of most of the organs of the adult fly are determined in the imaginal structures of the larvae (Cohen, Imaginal disc development, in The Development of *Drosophila melanogaster*, M. Bate and A. Martinez-Afias, eds. (Cold Spring Harbor Laboratory Press, Cold Spring Harbor, N.Y.), 747–841 (1993); Fristrom and Fristrom, The metamorphic development of the adult epidermis, in The Development of *Drosophila melanogaster*, M. Bate and A. Martinez-Afias, eds. (Cold Spring Harbor Laboratory Press, Cold Spring Harbor, N.Y.), 843–897 (1993)). Imaginal discs, specialized groups of undifferentiated epithelial cells that are recruited during embryogenesis, are formed in the first larval instar as integuments of the larval epidermis. Disc cells divide rapidly throughout the larval development and cease proliferating at the end of the third instar period. In leg, wing, and haltere discs, progression through the cell cycle stops in G2 phase 3–4 hours before puparium formation. It resumes 15–18 hours later (12–14 hours after pupariation) and then stops again in a defined spatial pattern after 12–14 hours (10–14 hours of pupal development) (Fain and Stevens, *Devel. Biol.* 92:247–258 (1982); Graves and Schubiger, *Devel. Biol.* 93:104–110 (1982); Schubiger and Palka, *Devel. Biol.* 123:145–153 (1987)). Although most of the dividing cells in the late larvae and in the early pupae are already committed to their adult fate, they do not develop a fully differentiated phenotype until growth arrest is firmly established. Thus, cell proliferation is temporally separated from cell differentiation, which takes place later during metamorphosis. Experiments with transplanted imaginal discs suggest that cessation of cell proliferation in these structures is controlled by mechanisms that, while intrinsic to the disc, are not completely cell-autonomous (Bryant and Schmidt, *J. Cell Sci. Suppl.* 13:169–189 (1990); Cohen, Imaginal disc development, in The Development of *Drosophila melanogaster*, M. Bate and A. Martinez-Afias, eds. (Cold Spring Harbor Laboratory Press, Cold Spring Harbor, N.Y.), 747–841 (1993)). The signaling pathways that control coordinated temporary growth arrest in larvae and pupae and subsequent terminal growth arrest in pupae and adults are not known, but they probably involve intercellular and intracellular second messenger molecules which have not yet been identified.

Transformation of imaginal precursors in adult structures during fly metamorphosis involves transition from cell proliferation to cell differentiation. Cessation of cell division is a necessary, although not sufficient, condition for cell differentiation to proceed. A temporary cytostasis occurs at the end of the larval period, and permanent arrest of cell division occurs during pupal development. NO, a diffusible messenger molecule, is capable of efficiently blocking cell division. Induction of NOS initiates a switch to growth arrest prior to differentiation of cultured neuronal cells (Peunova and Enikolopov, *Nature* 375:68–73 (1995)). Thus, NOS can act as a permissive factor, making the further development of the fully differentiated phenotype possible. Results described herein show that NOS acts as an antiproliferative agent during normal Drosophila development, indicating that NO is an important growth regulator in the intact developing organism.

Throughout larval development, there is a gradual and spatially-specific accumulation of NADPH-diaphorase activity in developing imaginal discs, reflecting an increase in overall NOS content. At the time temporary cytostasis is being established in imaginal discs, NADPH-diaphorase staining becomes particularly intense, and it gradually decreases during prepupal and pupal development. Besides the imaginal discs, other structures with intense NADPH-diaphorase staining include imaginal rings, histoblasts and the brain. These structures undergo radical changes during metamorphosis before giving rise to adult organs. Their development includes periods of rapid cell division alternating with periods of cytostasis, and thus must employ mechanisms for coordinated cessation of DNA synthesis and cell division in a spatially defined pattern. Since NO can prevent cell division and can diffuse and act within a limited volume, the ability of NO to act to induce coordinated growth arrest during Drosophila development was considered. Indeed, if NO actively exerts its antiproliferative activity during the development of imaginal discs, then inhibition of NOS before the temporary cytostasis is established at the end of the larval period could lead to the reversal of the arrest of cell division and induce additional divisions, which in turn could lead to increased size of structures of the body of the adult fly. Conversely, excessive or ectopic production of NO in larvae could cause premature cessation of cell division and lead to a reduction in the size of the structures in the adults.

Both predictions were confirmed in experiments described herein, in which NOS activity was manipulated in the developing fly. NOS inhibition in larvae caused an increase in the number of cells in some parts of the adult body and an increase in their size, whereas ectopic expression of the NOS transgene during development caused a decrease in the number of cells in some structures in the adult and a decrease in their size, probably by partial fusion and reduction. In the developing leg, the segments that were most often affected when NOS activity was inhibited and the segments that were most often affected when the activity was ectopically induced were nonoverlapping and complementary. Most importantly, their distribution matched the distribution of NOS in the imaginal discs, thereby supporting the hypothesis that NO plays a causative role in growth arrest in normal development.

The antiproliferative properties of NO suggest that NOS acts in development through its influence on DNA synthesis and cell division. The results described herein with BrdU incorporation in leg discs with elevated and diminished production of NO corroborate this position and suggest a direct link between synthesis of NO, number of S-phase cells, and the final size of the organ. In accordance with this idea, in many instances no BrdU incorporation was observed in regions highly enriched in NOS. The mechanisms for the NO-mediated arrest of the cell cycle (both temporary and terminal) are not clear, but they likely involve the conventional cellular machinery for growth arrest, e.g., cell cycle-dependent kinases and their inhibitors. Consistent with this, changes in expression of these proteins were observed when cultured cells were treated with NO. An intriguing feature of imaginal disc cells is that they stop dividing and accumulate in G2 phase in the late third instar, preceding the period of temporary cytostasis (Fain and Stevens, *Devel. Biol.* 92:247–258 (1982); Graves and Schubiger, *Devel. Biol.* 93:104–110 (1982); Schubiger and Palka, *Devel. Biol.* 123:145–153 (1987)). This parallels a tendency of NO-treated (Peunova and Enikolopov, *Nature* 375:68–73 (1995)) and NGF-treated (Buchkovich and Ziff, *Mol. Biol. Cell* 5:225–241 (1994)) PC12 cells to accumulate in G2 phase. Interestingly, imaginal discs are released from the G2 block and reenter S phase 12–15 hours after pupariation, at the time when diaphorase staining is diminished to low levels in adult flies. These correlations between imaginal discs cells and NO-treated cells support the idea that NO can be a major inducer of cytostasis in the cells of imaginal discs in the prepupal stage.

The final number of cells in an organ or a segment is determined both by cell multiplication and cell death, which the forming structures of the fly undergo as a normal step in development (especially at the late stages of pupal development). Results described herein indicate that the changes in the size of the leg segments after manipulation of NOS activity correlated directly with the changes in DNA synthesis and the number of dividing cells. Furthermore, no significant changes in apoptosis were detected in the larval and prepupal leg discs after inhibition or ectopic expression of NOS, compared with the control discs, when cell death was monitored by acridine-orange staining or by the TUNEL assay. This suggests that it is cell multiplication, rather than changes in programmed cell death that leads to the changes in the size of the appendage.

On the other hand, apoptotic death may conceal excessive cell proliferation in other developing organs. The effect of the absence of programmed cell death on potential excessive cell proliferation was also assessed. Transgenic flies were used in which programmed cell death in the developing eye was suppressed by recombinant p35, an inhibitor of apoptosis, to reveal excessive proliferation after NOS inhibition. Under these circumstances, several cell types and structures are overrepresented, the most noticeable change being an overall increase of the size of the eye due to the increased number of ommatidia. In addition, other cell types (e.g., secondary and tertiary pigment cells, cone cells, and cells of the bristles) proliferated after NOS inhibition to levels higher that those achieved by blocking apoptosis by p35 (Hay et al., *Development* 120:2121–2129 (1994)). These data demonstrate that the removal of suppressive influence of NO leads to an increase in the size of the adult organ, unless this effect is masked by programmed cell death, and indicate that final cell number in the adult organ is under dual control by both cell proliferation and programmed cell death. Furthermore, these data provide independent support for the hypothesis that NO directly regulates cell number during development.

After inhibition of NOS with either of two structurally unrelated compounds, excessive growth was observed in most of the structures of the adult flies that derive from imaginal discs and histoblasts, to varying extents for different organs. The most obvious changes were observed in the segments of the legs whose primordia showed the highest levels of NOS. There did not appear to be any substantial number of instances in which a duplication of a larger structure (for example, segments of the legs or wings) occurred. This indicates that extra proliferation of cells under the influence of NOS inhibitors occurs after the developmental fate is determined for most of the cells in the imaginal discs. This suggests that in most cases NO may be more important for the induction of growth arrest and subsequent differentiation of already committed cells than for the developmental commitment and establishment of the cell identity in the embryo or larvae.

Only some of the axes of the developing structures were affected by manipulations of the NOS activity. For instance, in developing legs only the anteroposterior and the dorsoventral axes, but not the proximodistal axis, were affected by inhibition of NO production. In contrast, when NOS was ectopically expressed, only the proximodistal axis was affected. These results suggest that a gradient of NO may be involved in the process of establishing the polarity of the axes of the developing organ.

Thus, these results demonstrate that inhibition of NOS in larvae leads to enlargement of organs in adults and, conversely, that ectopic expression of NOS in larvae leads to a reduction in the size of organs in adults. Also, the distribution of affected segments in the adult leg corresponds to the distribution of NOS in the larvae, and the changes in segment size can be directly correlated to changes in DNA synthesis in imaginal discs after manipulations of NOS activity. The increased cell proliferation that occurs in response to NOS inhibition is masked in some structures by programmed cell death, and it can be revealed by suppressing apoptosis. Taken together, these results demonstrate that activation of NOS is a crucial step in Drosophila development. They confirm that NO acts as an antiproliferative agent during cell differentiation and organism development and controls the cell number in an intact developing organism.

NOS expression can be induced to high levels in a large number of tissues and cell types by appropriate stimulation (Bredt and Snyder, *Annu. Rev. Biochem* 63:175–195 (1994); Forstermann et al., *Adv. Pharmacol.* 34:171–186 (1995)). In most cases, the pattern of NOS distribution in a developing organism differs strongly from the distribution in the adult organism. Furthermore, transient elevation of NOS expression in a given tissue often coincides with the cessation of division of committed precursor cells. The developing mammalian brain provides an especially apt demonstration of this (Bredt and Snyder, *Neuron* 13:301–313 (1994); Blottner et al., *Histochem. J.* 27:785–811 (1995)). A strong elevation of NOS activity in the developing cerebral cortical plate and hippocampus at days 15–19 of prenatal development correlates with the timecourse of cessation of precursor cells proliferation, tight growth arrest, and cell differentiation; notably, NOS activity goes down after the proliferation of committed neuronal precursors is completed. NOS levels are also transiently increased in developing lungs, bones, blood vessels, and nervous system (Blottner et al., *Histochem. J.* 27:785–811 (1995); Collin-Osdoby et al., *J. Cell Biochem.* 57:399–408 (1995); Cramer et al., *J. Comp. Neurol.* 353:306–316 (1995); Shaul, *Adv. Pediatr.* 42:367–414 (1995); Wetts et al., *Dev. Dyn.* 202:215–228 (1995)). Elsewhere, NOS activity is greatly elevated in regenerating tissues when cessation of cell division is crucial for prevention of the unregulated growth (Roscams et al., *Neuron* 13:289–299 (1994); Blottner et al., *Histochem. J.* 27:785–811 (1995); Decker and Obolenskaya, *J. Gastroenterol. Hepatol.* 10 *Suppl* 1:2–7 (1995); Hortelano et al., *Hepatology* 21:776–786 (1995)). In all these cases, a transient elevation of NOS activity might trigger a switch from proliferation to growth arrest and differentiation, thus contributing to the proper morphogenesis of the tissue and the organ.

Results described herein support the position that production of NO is required during embryonic development and during tissue regeneration in the adult organism for the proper control of cell proliferation. The antiproliferative properties of NO are particularly important in situations in which terminal differentiation of committed cells is temporally separated from cell proliferation and is strictly dependent on cessation of cell division. Given the multiplicity of the NOS isoforms and their overlapping tissue distribution, it is conceivable that any group of cells in the embryo and fetus can be exposed to NO action. Furthermore, recent data showing that NO can be transferred within the organism by hemoglobin (Jia et al., *Nature* 380:221–226 (1996)) raise the possibility that a developing mammalian embryo can be also supplied with NO exogenously by the mother.

NO is a readily difusible molecule, and it may therefore exert its antiproliferative properties not only in the cell that produces it but in the neighboring cells as well (Gally et al., *Proc. Natl. Acad. Sci. USA* 87:3547–3551 (1990)). This property is important when one considers mechanisms for the coordinated development of a group of neighboring cells committed to form a particular structure. These cells have to generate an intrinsic signal that tells them to stop dividing in a coordinated fashion after they have reached a certain number. This cooperation and coordination is achieved in many instances by tightly controlled paracrine regulation, which involves signaling between adjacent cells via gap junctions or secreted proteins. Results described herein show that yet another way of coordinating developmental decisions in groups of cells is by diffusible antiproliferative second messenger molecules, which can spread without a need for surface receptors or specialized systems for secretion and exert their influence within a limited domain. An efficient source of readily diffusible molecules may induce synchronized changes in the adjacent cells within a limited volume of a tissue. Moreover, several adjacent cells producing easily diffusible antiproliferative messenger molecules may share the total pool of these molecules produced by the neighbors as well as by themselves. If a particular threshold level of a signal is needed to initiate a signaling chain that eventually leads to growth arrest, then the cells in this group could stop dividing when a certain number of cells and, therefore, a certain local concentration of messenger molecules, is reached. In this way, by organizing groups of cells in functional clusters and coordinating their decisions on proliferation and differentiation, NO instruct the developing structures to terminate their growth when they attain the appropriate size and shape, and, thus, participate in tissue and organ morphogenesis.

As also described herein, the role of NO in hematopoiesis was examined. To demonstrate the presence of NOS in the bone marrow (BM) cells, BM from adult mice was tested for the NDPH-diaphorase activity of NOS (which reflects the distribution of the total enzyme activity in a tissue). It was found that BM contains a substantial proportion of cells (up to 12%) with strong diaphorase staining. The morphology of the NADPH-diaphorase cells suggests that they are largely of the granulocyte-macrophage lineage at different stages of differentiation. This is in accordance with numerous data showing that NOS is present in the cells of the myeloid lineage, and can be induced to high levels by appropriate stimulation.

A mouse model of syngeneic BM transfer was used to evaluate the role of NO in hematopoiesis. Mice were irradiated to inhibit hematopoiesis in the recipient animal, BM was transplanted from syngeneic animals, and the animals were treated with specific NOS inhibitors. This procedure permits the proliferation, differentiation and survival of only the transplanted cells. To study the changes in hematopoiesis introduced by NOS inhibitors, the colonies in the spleen were monitored to test the differentiation of erythroid cells, and the formation of colonies on the membranes placed in the peritoneal cavity of the recipients were monitored to test the differentiation of cells of the granulocyte-macrophage lineage. The role of NO on hematopoiesis was tested by injecting the animals with the specific and structurally unrelated NOS inhibitors L-nitroarginine methyl ester (L-NAME), and 2-ethyl-2-thiopseudourea (ETU). The inactive enantiomer D-NAME was used as a control. Animals were sacrificed and the number and composition of colonies in the spleen (reflecting the cells which have undergone erythroid differentiation) and colonies on the membranes (reflecting the cells that have undergone myeloid differentiation) were studied.

Taken together, the results of these studies indicate that NO modulates hematopoiesis after BM transplantation. This confirms the role of NO as a major regulatory factor in the organism controlling the balance between proliferation and differentiation. This also shows that manipulation of NO levels may be used for therapeutic intervention to increase the number of undifferentiated hematopoietic cells after BM transplantation; change the ratio of cells undergoing erythroid or myeloid differentiation; and interfere or suppress graft-versus-host disease, which is a major cause of mortality in patients undergoing BM transplantation.

Most of the tissues and organs in the adult organism are constantly undergoing regeneration and renovation, going through phases of rapid proliferation, determination, growth arrest, differentiation, and often, programmed cell death. Many human diseases are caused by improper or incomplete differentiation steps, resulting in the loss of function of a particular tissue or organ. This suggests that these diseases can be treated, and, furthermore, proper function of the affected tissues and organs can be restored by targeting and manipulating cell and tissue differentiation.

This work described herein, demonstrating the role of NO in cell proliferation and differentiation in an organism, provides for various therapeutic applications in humans and other mammals. In particular, this NO-based approach can be focused on renewable and regenerating tissues, such as blood, bone, skin, and digestive epithelium. Additionally, a similar strategy can be used to repopulate organs with normally nondividing cells such as muscle and nerve cells.

The work described herein can also be used to enhance gene therapy methods. For example, NOS can be used to drive a population of cells into the S phase wherein the cells are replicating. As known in the art, replicating cells are more responsive to gene therapy methods (e.g., introduction of genes via live vectors) than non-replicating cells. Thus, the present invention provides for a method of converting cells into a state which renders the cells more receptive to gene therapy methods, wherein the cells are contacted with a NO inhibitor (e.g., NOS inhibitor). Conversely, the present invention provides for a method of converting cells into a state which renders the cells resistant to gene therapy methods. That is, the present invention provides for a method of converting cells into a state which renders the cells more resistant to gene therapy methods, wherein the cells are contacted with NO and/or a NO enhancer (e.g., NOS enhancer).

The results of work described herein support the ability of NO to act as a crucial regulator of hematopoiesis after bone marrow transplantation (BMT). NO regulates maturation of both erythroid and myeloid cell lineages. By interfering with NO production in the recipient animal after BMT, the number of undifferentiated stem and blast cells which are then capable of further differentiation along the erythroid or myeloid lineages can be dramatically increased. The blast cells' enrichment reaches 80-fold for the myeloid lineage, and 20-fold for the erythroid lineage. The data described herein demonstrates that manipulations of NOS activity and NO levels during hematopoiesis can be used for therapeutic purposes to influence self renewal and differentiation of hematopoietic stem cells, and to replace damaged or defective cells. Areas of application include enhancement of blood cell and myeloid cell formation following high dose chemotherapy in cancer treatment; improved engraftment following bone marrow or stem cell transplantations, and gene therapy; stem cell therapy by amplifying the undifferentiated cells of erythroid and myeloid lineages and applying appropriate factors to induce terminal differentiation; and regulation of formation of various blood cell components for treating hematological and autoimmune disorders.

The data also shows that changing the levels of NO production interferes with osteoblast and chondrocyte differentiation. These results show that manipulation of NO production can regulate growth and differentiation of osteoblasts, chondrocytes, or mesenchymal stem cells. This can be used for amplification and further differentiation of cells in the injured tissue, or for cell implants (in combination with biocompatible carriers, if necessary). Thus, an NO-based approach can be used for regeneration therapy of the damaged tissue, post injury repair, age related diseases such as osteoporosis and osteoarthritis, and for reconstituting marrow stroma following high dose cancer chemotherapy.

In addition, the data shows that changing the levels of NO production interferes with keratinocyte differentiation. The results described herein demonstrate that regulation of NO production can be used when increased proliferation and subsequent differentiation of skin tissue is required (e.g., during burns and wound healing). Furthermore, NO can be used to control disorders caused by hyperproliferation of keratinocytes during psoriasis. Yet another potential application is to use NO-based preparations as exfoliant agents in cosmetic therapy.

No has been shown to act as a regulator of cell differentiation in neuronal cells. It has been demonstrated that NO regulates brain development in animals and contributes to controlling the size of the brain in intact animals.

It has also been demonstrated that in certain contexts NO mediates the survival effects of growth factors by activating an antiapoptitic program and can protect neuronal cells from death. Combined, these studies of the role of NO in neurons suggest that NO may be used to control proliferation and subsequent differentiation of nerve cells in replacement therapy after neurodegenerative disorders caused by aging (e.g., Alzheimer's or Parkinson's), stroke, or trauma.

NO is actively produced in smooth muscle cells of the blood vessels and is subject to complex physiological regulation. These cells are highly susceptible to suppression of DNA synthesis by NO. The very strong antiproliferative activity of NO can be used for inhibition of smooth muscle cells proliferation and neointima formation for treatment of restenosis following angioplasty.

In addition, NO-based therapy has application for treatment of ailments characterized by destruction of specific sets of cells. This includes hepatocyte regeneration after toxic injury of the liver, treatment of reproductive system disorders, and administration of differentiated pancreatic tissue for treatment of type 1 diabetes.

The methods of the present invention can be carried out in vivo or ex vivo. Administration of the NO inhibitor, NO enhancer and/or agent which induces differentiation can performed using various delivery systems known in the art. The routes of administration include intradermal, transdermal, intramuscular, intraperitoneal, intravenous, subcutaneous, oral, epidural and intranasal routes. Any other convenient route of administration can be used such as, for example, infusion or bolus injection, or absorption through epithelial or mucocutaneous linings. In addition, the NO inhibitor, No enhancer and/or agent which induces differentiation can be administered with other components or biologically active agents, such as adjuvants, pharmaceutically acceptable surfactants, excipients, carriers, diluents and vehicles. Administration can be systemic or local, e.g., direct injection at the site containing the cells to be targeted.

The NO inhibitor, NO enhancer and/or agent which induces differentiation can be administered as proteins (peptides) and/or genes (polynucleotides) encoding such proteins or peptides. In the embodiment, in which the NO inhibitor, NO enhancer and/or agent which induces differentiation are protein or peptides, they can be administered by in vivo expression of genes or polynucleotides encoding such into a mammalian subject. Several expression systems, such as live vectors, are available commercially or can be reproduced according to recombinant DNA techniques for use in the present invention.

The amount of No inhibitor, NO enhancer and/or agent which for use in the present invention which will be effective in the treatment of the particular disorder or condition will depend on the nature of the disorder or condition, and can be determined by standard clinical techniques. The precise dose to be employed in the formulation will also depend on the route of administration and the seriousness of the disease or disorder, and should be decided according to the judgement of the practitioner and each patient's circumstances.

The following Examples are offered for the purpose of illustrating the present invention and are not to be construed to limit the scope of this invention. The teachings of all references cited herein are hereby incorporated herein by reference.

EXAMPLES

Example 1
Nitric Oxide Regulates Cell Proliferation During Drosophila Development Drosophila Stocks Drosophila melanogaster Oregon R strain was used for most of the experiments described. Transgenic GMR-P35 flies (3.5 and 2.1 alleles, Hay et al., *Development* 120:2121–2129 (1994)) were a generous gift from B. Hay and G. M. Rubin. Transgenic flies carrying mouse macrophage NOS (NOS2) gene under heat-shock promoter (hs-mNOS20(2) and hs-mNOS 15(2) alleles) were generated by P-element-mediated germline transformation. A 4100 base pair NotI fragment from the plasmid CL-BS-mac-NOS containing the entire mouse macrophage NOS gene (Lowenstein et al., *Proc. Natl. Acad. Sci. USA* 89:6711–6715 (1992)) was cloned into the NotI site in the P element vector pP(CaSpeR-hs) (Thummel and Pirrotta, *Drosophila Information Service* 71:150 (1992)), placing it under the control of the Drosophila hsp70 promoter. The construct was coinjected into embryos (Spradling, P element-mediated transformation, in Drosophila: A practical approach, D. B. Roberts, ed. (Oxford: IRL Press) 60–73 (1986)) with the helper P element phs-II-Δ2–3 (Misra and Rio, *Cell* 62:269–284 (1990)). A set of two independent, homozygous transformants were established. Expression of the NOS2 transgene after heat-shock treatment of larvae and adult flies was confirmed by diaphorase staining and by protein and RNA analysis. In control experiments, identical regimens of heat-shock treatment of nontransformed flies did not induce any anatomical changes per se.

Histochemistry and Electron Microscopy

NADPH-diaphorase staining was performed as described by Dawson et al., *Proc. Natl. Acad. Sci. USA* 88:7797–7801 (1991) and Hope et al., *Proc. Natl. Acad. Sci. USA* 88:2811–2814 (1991), with minor modifications. Fixation-insensitive NADPH-diaphorase staining reflects activity of various NOS isoforms in mammals and Drosophila. Imaginal discs were mounted in 80% glycerol and photographed in a Zeiss Axiophot microscope under Nomarski optics. Cobalt-sulfide staining of the pupal retinae was carried out as described by Wolff and Ready, *Development* 113:825–839 (1991). BrdU labeling to identify cells in S phase was performed essentially as described by Schubiger and Palka, *Devel. Biol.* 123:145–153 (1987) and by Baker and Rubin, *Devel. Biol.* 150:381–396 (1992), with minor modifications. Imaginal discs were removed, rinsed, and incubated in Schneider's media in 50 μg/ml solution of BrdU for 30–40 minutes at room temperature. They were fixed in 4% formaldehyde, treated with 1:1 mixture of heptane and formaldehyde, rinsed, depurinated by 1M HCl, blocked by 1% sheep serum, and incubated with anti-BrdU antibodies (Beckton-Dickinson). After extensive washing, discs were incubated with fluoresceine-coupled anti-mouse secondary antibodies (Boehringer-Mannheim). After rinsing, individual imaginal discs were dissected away, dehydrated in ethanol, and mounted in Vectashield mounting media (Vector Laboratories). Scanning electron microscopy was performed at the SUNY Stony Brook Microscopy Center essentially as described by Kimmel et al., *Genes Devel.* 4:712–727 (1990). The number of ommatidia was determined both by analyzing series of scanning electron micrographs and by analyzing adult heads under the blue fluorescent light in a Zeiss Axiophot microscope.

Microinjection of Larvae

For inhibition of NOS, third instar larvae were injected with L-nitroarginine methyl ester (L-NAME), its inactive enantiomer D-nitroarginine methyl ester (D-NAME) (both from Sigma), and 2-ethyl-2-thiopseudourea (ETU; Calbiochem). Chemicals were dissolved in Schneider's solution at concentrations of 0.1M for L-NAME and D-NAME and 0.01M for ETU and mixed with Freund's adjuvant (Sigma) in 1:3 ratio. Amounts of 5–10 nl were microinjected in staged late third instar using a glass needle. Timing of the injection of NOS inhibitors that gave the highest efficiency (as determined by the changes in the phenotype of the adults) was determined in trial experiments and was found to be most efficient when performed 5–12 hours before pupanation. This treatment did not affect the onset of pupanation and hatching.

Ectopic Expression of NOS

For regulated ectopic expression of NOS, larvae carrying the mouse NOS2 cDNA under the control of Drosophila heat-shock promoter were treated with heat shock at 36° C. for 40 minutes within the first hour after puparium formation. For BrdU labeling experiments, third instar larvae were treated with heat shock 5–8 hours before puparium formation.

Results

NOS is Expressed in Imaginal Discs During Larval Development

At the end of the third instar, cells of imaginal discs undergo temporary cell cycle arrest. Cytostasis is released 12–14 hours after pupariation and is established once again (permanently) in the late pupae and the pharate adult. The ability of NO to reversibly halt cell division and establish temporary growth arrest makes it a plausible candidate for mediating cytostasis in imaginal discs. To investigate this possibility, imaginal discs of the third instar and early pupae were examined for NOS presence. Drosophila NOS (dNOS) gene, which is preferentially expressed in the adult head, has recently been cloned and characterized (Regulski and Tully, *Proc. Natl. Acad. Sci. USA* 92:9072–9076 (1995)). However, different NOS-related mRNA species are present in the embryo, larvae and adult flies. These mRNAs may be produced by the cloned dNOS gene or by other potential Drosophila NOS genes, making the detection of the relevant RNA species difficult. Therefore, to visualize the expression of NOS in Drosophila during larval development, histochemical staining for the NADPH-diaphorase (reduced nicotinamide adenine dinucleotide phosphate-diaphorase) activity of NOS was used, which reflects the distribution of the total enzyme activity in a tissue (Dawson et al., *Proc. Natl. Acad. Sci. USA* 88:7797–7801 (1991); Hope et al., *Proc. Natl. Acad. Sci. USA* 88:2811–2814 (1991); Muller, *Eur. J. Neurosci.* 6:1362–1370 (1994)).

NADPH-diaphorase staining was observed in all imaginal discs, imaginal rings, histoblasts and the brain of the larvae, beginning in the third instar. Staining became more intense as development proceeded, and in late third instar larvae and early pupae, a highly specific and reproducible pattern of very intense staining was evident. In the leg imaginal disc NADPH-diaphorase staining was initially seen at the very beginning of the third instar. Staining was confined to the center of the disc, corresponding to the presumptive distal tip of the leg. As the discs matured, diaphorase staining intensified, and in the late third instar it nearly obliterated the distinction between individual concentric rings of epithelial folding normally seen in axial view. At the end of the third instar stage, the staining of the center of the disc (distal tip), which stained most darkly at the beginning of the third period, was weaker in comparison with the surrounding cells. Later in development, when the discs began to evert in the prepupae, diaphorase staining of the forming leg became less intense, and a distinct characteristic pattern of staining of individual segments became evident. At 2–4 hours after puparium formation, intense NADPH-diaphorase staining was observed in the presumptive tibia, first and second tarsal segments, and the proximal part of the fifth tarsal segment of the forming leg. Staining was much weaker in the third and fourth segments, and areas of intense staining were unevenly distributed throughout the regions of presumptive femur. Weak staining was also present in the coxa and body wall. The progression of staining patterns throughout the larval development was highly specific and reproducible. The staining of the imaginal discs corresponding to the first, second and third pairs of legs was very similar. As, with the leg imaginal discs, other imaginal discs, imaginal rings and histoblasts exhibited increasingly intense NADPH-diaphorase staining as larval development proceeded. Wing, eye, haltere and genital discs in the third instar had distinct and reproducible patterns of intense staining, which gradually decreased in a specific spatial pattern during early pupal development.

These results demonstrate that there is a gradual and specific accumulation of NOS in developing imaginal discs, which reaches highest levels at the time when the progression through the cell cycle slows down.

Synthesis of DNA is Affected By Manipulations of NOS Activity

If NO acts as an antiproliferative agent during Drosophila development at stages when the cells of imaginal discs enter temporary cytostasis, then its action might directly affect DNA synthesis in the discs. Inhibition of NOS would then be expected to relieve the block and increase the number of cells in S-phase; conversely, high levels of NO would lead to a decrease in the number of dividing cells. To test this hypothesis and to map the extent and distribution of the antiproliferative effect of NO, DNA synthesis in larval and prepupal discs was monitored while the levels of NOS activity were manipulated. To inhibit NOS activity, specific NOS inhibitors were injected into developing larvae. To increase the levels of NOS, expression of NOS transgene was induced in transformed larvae carrying the mouse NOS2 cDNA gene (Lowenstein et al., *Proc. Natl. Acad. Sci. USA* 89:6711–6715 (1992)) under the control of the heat shock promoter. NOS2 is a calcium-independent form of NOS that is capable of efficient constitutive NO production. Imaginal discs were labelled with 5-bromo-deoxyuridine (BrdU), and the extent and distribution of labeling of S-phase nuclei in leg imaginal discs from larvae after inhibition of NOS, from NOS2 transformants after heat shock induction, and from control untreated larvae were compared. The data show that there were significantly more BrdU-labeled cells in imaginal discs of larvae in which NOS activity was suppressed by L-nitroarginine methyl ester (L-NAME) than in control untreated larvae (or larvae treated with the inactive isomer D-NAME). The data also show that there were significantly more BrdU-labeled cells in imaginal discs of flies in which NOS was inhibited than in control flies. In contrast, there were markedly fewer BrdU-labeled cells in imaginal discs from induced NOS-transformed flies than in uninduced controls. At the same time, these changes in the number of BrdU-labeled cells after inhibition or ectopic expression of NOS appeared to be evenly distributed over the entire disc.

These data indicate that modulation of NOS activity affects the number of cells in S phase in imaginal discs, which is consistent with the observations that NO suppresses DNA synthesis and cell division.

Inhibition of NOS Results in Hypertrophy of Leg Segments

The highest levels of diaphorase staining occur during the period of development when DNA synthesis and the rate of cell division in most of the imaginal disc cells slow down. The strong anti-proliferative properties of NO and the specific pattern of diaphorase staining seen in mature imaginal discs implied that NO might act as a growth arrest agent in these structures, capable of inhibiting DNA synthesis and supporting temporary cytostasis during the switch to metamorphosis. If NO indeed acts as an anti-proliferative agent during the late stages of larval development, then inhibition of NOS might result in excessive growth of organs and tissues, whereas ectopic overexpression of the NOS gene might have the opposite effect.

To test this hypothesis, NOS activity was inhibited by injecting specific NOS inhibitors in the developing larvae at the end of the third instar, several hours before metamorphosis. Most of the larvae completed metamorphosis successfully, giving rise to adult flies within the normal time frame. The resulting adults differed from normal flies in many respects, the most dramatic being enlargements of the appendages and other structures of the fly body. The changes included a) hypertrophy of the femur, tibia and the segments of the tarsus; b) overgrowth of the tissues originating from the genital disc; in extreme cases, these cells contributed to more than one-quarter of the fly body; c) an increase of the overall surface of the wings; d) overgrowth of the cells of tergites and sternites; e) hypertrophy of the humerus; f) occasional duplications of some areas of the eye; g) occasional realformation of genital structures, legs and eyes; and h) occasional ectopic formation of misplaced body structures.

The changes were most profound in, and most often affected the legs of, the adults. The hypertrophy was particularly strong in the third pair of legs, where the diameter of certain segments increased 3–4 fold. The number of bristles and the number of rows of bristles also increased, confirming that hyperproliferation of the cells had occurred. The leg segments most strongly affected were those (first and second tarsal segments, tibia, and femur) whose primordia had the highest levels of NOS at the larval and prepupal stages. The changes affected mainly the anteroposterior and dorsoventral but not the proximodistal axes, so that the length of the affected segments remained the same. Identical changes were observed when two structurally unrelated inhibitors of NOS, 2-ethyl-2-thiopseudourea (ETU) and L-NAME (but not D-NAME) were used, indicating that the observed effect resulted specifically from blocking NOS activity.

In summary, these data show that inhibition of NOS at the late stages of larval development results in excessive cell proliferation and increased size of the structures of the body of the adult fly.

Ectopic Expression of a Mouse NOS Transgene Results in Reduced Size of Leg Segments The ability of NO to inhibit DNA synthesis and cell proliferation suggests that overexpression of NOS in developing larvae may lead to diminished cell proliferation in the imaginal discs and to a reduction in the size of organs of the adult fly. Transformed flies that express the mouse NOS2 transgene under the control of the heat-shock promoter were tested. Transgenic larvae were heat-shocked within one hour after pupariation to induce ectopic expression of NOS before the final cell divisions take place. This resulted in a reduction in the size of the limbs of the fly. The distal segments of the legs were affected most frequently and to the greatest degree. In extreme cases, the whole tarsus was shortened 1.5–2 fold, and the third, fourth and fifth segments were fused together with poorly defined boundaries. The number of bristles in a row on the affected segments also decreased, although the number of rows did not change. The segments of the adult leg most often affected by the overexpression of NOS (third, fourth and fifth tarsal segments) were those that were not affected by the NOS inhibitors and whose precursors exhibited particularly low levels of diaphorase staining in the early prepupal stages. The most terminal structures of the appendage, including the tarsal claw, remained intact in these defective legs. This suggests that the observed reduction in size was due to incomplete growth of the distal area of the developing appendage, rather than to complete loss of its distal structures. In contrast to the results on NOS inhibition, the changes affected only the proximodistal axis, while the diameter of the affected segments remained the same. In addition to the reduction in the size of the leg segments, changes included a decrease in the overall surface of the wings, cuts in the wings, and reduced size of tergites and sternites.

These results support the conclusion that ectopic expression of NOS at the late stages of larval development results in a decrease in cell proliferation and a reduction in the size of the structures of the body of the adult fly.

Inhibition of Apoptosis Unmasks Excessive Proliferation

In leg imaginal discs, the changes in the number of S-phase nuclei after manipulation of NOS activity directly correlated with the changes in the size of the adult limbs. However, in the eye imaginal disc, an increase in the number of cells in S-phase was consistently detected after inhibition of NOS, but the resulting adult eye usually appeared normal. The possibility that the apparently normal eye phenotype occurred as a result of programmed cell death, which counteracts excessive cell proliferation induced by NOS inhibition and restores the normal number of cells in the eye during metamorphosis, was tested. To suppress programmed cell death, GMR-P35 flies were used (Hay et al., *Development* 120:2121–2129 (1994); donated by Drs. B. Hay and G. Rubin) in which apoptosis in the developing eye is largely prevented by expression of recombinant baculovirus p35 protein. p35 is a strong inhibitor of apoptosis, which acts by inhibiting the interleukin 1B-converting enzyme-like proteases and is able to prevent apoptosis in multiple contexts. GMR-P35 flies express p35 under the transcriptional control of multimerized glass-binding site from the Drosophila Rhl promoter. Glass promoter directs expression of the transgene in all cells in and posterior to the morphogenetic furrow in the eye disc (Ellis et al., *Development* 119:855–865 (1993)).

When NOS was inhibited in GMR-P35 larvae, the eyes of the adult flies showed numerous changes, reflecting the excessive proliferation of various cell types in the developing eye. The most dramatic of these changes was in the number of ommatidia in the adult eye, which increased from the nearly invariant complement of 750 in wild type flies (747+/−4) and untreated GMR-P35 flies (748+/−6), to nearly 820 (818+/−21) after NOS inhibition in GMR-P35 flies. This, together with the elevated number of cells per ommatidium, caused an increase in the overall size of the eye. Other changes in p35-expressing flies after inhibition of NOS compared with the control GMR-P35 flies included a) more ommatidia with an irregular shape (perhaps, because of the uneven increase in the number of various cell types); b) more ommatidia with an irregular arrangement of the rows; and c) more ommatidia of a smaller size.

Another manifestation of the inhibition of NO production in GMR-P35 flies was an increase in the number of pigment, cone, and bristle cells. Wild type ommatidia contain, in addition to eight photoreceptor cells, a set of four cone cells and two primary pigment cells, surrounded by an array of six secondary pigment cells, three tertiary pigment cells, and three bristles (Wolff and Ready, Pattern formation in the *Drosophila retina*, in The Development of *Drosophila melanogaster*, M. Bate and A. Martinez-Arias, eds. (Cold Spring Harbor Laboratory Press, Cold Spring Harbor, N.Y.), 1277–1326 (1993)). The number of photoreceptor and accessory cells is normally constant, and variations in this arrangement in the eyes of the normal flies are very rare. In GMR-P35 flies, the number of secondary and tertiary pigment cells was increased from 12 to 25 (25+/−4) cells per sample area (defined as described in Hay et al., *Cell* 83:1253–1262 (1995)) as a result of suppressed programmed cell death. Inhibition of NOS in these flies resulted in a further increase in the number of secondary and tertiary pigment cells to more than 35 (36+/−8) per sample area. This number exceeds the maximal number of pigment cells saved from programmed cell death in untreated GMR-P35 flies and suggests that extra pigment cells arise as a result of excessive cell proliferation caused by inhibition of NOS combined with suppression of cell death caused by p35.

The number of ommatidia with extra primary pigment cells in GMR-P35 flies after inhibition of NOS was also increased in comparison with control flies, although it only slightly exceeded the levels in untreated GMR-P35 flies. Furthermore, the number of bristles was increased in some areas of the eye in GMR-P35 flies after NOS inhibition, up to 4–5 per ommatidium instead of the three seen in normal flies and untreated GMR-P35 flies, and these were often mislocated. Similarly, the number of cone cells was increased from four in normal and untreated GMR-P35 ommatidia to five and six in many ommatidia of GMR-P35 flies after NOS inhibition. Clusters of ommatidia were also found which contained one, two, or three cone cells, which may correspond to improperly formed supernumerary ommatidia that did not attain the proper set of cells.

Thus, prevention of apoptosis by baculovirus p35 protein in the developing eyes of transgenic flies revealed excessive proliferation of various cell types after NOS inhibition in larvae, which was otherwise masked by programmed cell death in the larvae and pupae.

Example 2

Nitric Oxide Regulates Hematopoiesis in Animals Erythroid Differentiation

To study the formation of cell of the erythroid lineage in the spleen of the irradiated recipient mice, the animals (females of F1 CBAxC57B1 hybrids weighing 22–24 g) were treated with 750 cGy total body irradiation within 3–4 hours before transplantation. This dosage was tested to be enough for complete suppression of hematopoiesis in the irradiated recipient animals. BM cells were flushed from the femurs of syngeneic donors and injected intravenously ($10^5$ BM cells per mice) in the recipients. The animals received twice a day injections of 100 mg/kg of L-NAME and D-NAME and 10 mg/kg of ETU for 7–10 days. Mice were analyzed 9–10 days after transplantation.

The differentiation status of the colonies in the spleen was evaluated by morphological criteria and by immunohistochemical tests for the presence of receptors to various cytokines, which are present only at specific stages of the erythroid cells' maturation. The analysis of the colonies in the spleen of control animals and animals treated with inactive enantiomere D-NAME (Table 1) showed that in agreement with numerous data, most of the colonies in the spleen (>60%) contained erythroid colonies, smaller fractions contained undifferentiated blasts cells (14%) or both erythroid and blast cells (13%), and small fractions of colonies contained megakaryocytes (7.5%) and granulocytes (4%). In contrast, when animals were treated with NOS inhibitors after BM transplantation, most of the colonies in the spleen contained undifferentiated blast cells (up to 85% of blast cells colonies and mixed blast-erythroid cells colonies). Erythroid colonies comprised only 15% of the total number of colonies, and the megakaryocyte and granulocyte colonies were not detectable. The results were similar with two structurally unrelated NOS inhibitors, confirming the specificity of their action. Thus, prolonged treatment of recipient mice after BM transfer with NOS inhibitor, reversed the ratio of blast cells-containing colonies to the erythroid cells-containing colonies almost 16 fold, effectively preventing erythroid differentiation.

TABLE 1

Formation of hemopoietic colonies in spleens of irradiated mice after injection of NOS inhibitors.

|  | blast cell colonies | blast cell and erythroid cells colonies | erythroid colonies | megakaryocyte colonies | granulocyte colonies |
|---|---|---|---|---|---|
| Experiment | 54.6% | 30.25% | 15.12% | — | — |
| Control | 14.3% | 12.9% | 61.22% | 7.48% | 4.08% |

Myeloid Differentiation

To study the formation of the cells of the myeloid lineage, cellulose acetate membranes were implanted in the peritoneal cavity of mice. After 7 days, when a layer of fibroblasts had covered the membranes, the mice were irradiated as described above. BM cells from syngeneic donors were injected ($10^5$ BM cells per mice) in the peritoneal cavity of the recipients. Animals received injections of NOS inhibitors as described above. Membranes with growing colonies were isolated and analyzed 7–8 days later.

The differentiation status of the colonies in the spleen was evaluated by morphological criteria, myeloperoxidase reaction, and by immunohistochemical tests for the presence of receptors to various cytokines, which are present only at specific stages of the myeloid cells' maturation. The analysis of the colonies on the membranes in control animals and animals treated with inactive enantiomere D-NAME (Table 2) showed that in agreement with numerous data, most of the colonies (92%) contained granulocytic colonies. A much smaller fraction contained undifferentiated blasts cells (6%), and a very small fraction of colonies contained erythroid cells (1.3%). In contrast, when animals were treated with NOS inhibitors after BM transplantation, most of the colonies on the membranes (up to 85%) contained undifferentiated blast cells. Colonies with differentiated cells of the granulocyte lineage comprised only 15.6% of the total number of colonies, and a negligible fraction of the colonies (<0.5%) contained erythroid cells. The results were similar with two structurally unrelated NOS inhibitors, confirming the specificity of their action. Thus, prolonged treatment of recipient mice after BM transfer with NOS inhibitor, reversed the ratio of blast cells-containing colonies to the granulocytic colonies almost 80-fold, effectively preventing myeloid differentiation.

TABLE 2

Formation of hemopoietic colonies on cellulose acetate in the peritoneal cavity of irradiated mice after injection of NOS inhibitors.

|  | blast cell colonies | granulocytic colonies | erythroid colonies |
|---|---|---|---|
| Experiment | 84.46% | 15.6% | — |
| Control | 6.34% | 92.3% | 1.34% |

Differentiation Status of Transplanted BM Cells

To study the stage to which the transplanted cells have progressed, colonies in the spleen and on the membranes were tested with specific antibodies for receptors of various growth factors. This analysis permits one to visualize and evaluate the stage of the multistep differentiation process that eventually leads to erythroid or myeloid differentiation. We have used antibodies specific for the receptors to interleukin 3(IL-3-R), granulocyte-macrophage colony stimulating factor (GM-CSF-R), granulocyte colony stimulating factor (G-CSF-R) and erythropoietin (EpoR). The appearance of each of these receptors marks a specific stage in hematopoiesis.

The results of the analysis demonstrate that the blast cells in the spleen colonies (representing erythroid differentiation) have accumulated mostly at the stage of differentiation where they have already acquired the receptor for IL-3, but not for erythropoietin, GM-CSF or G-CSF, whereas the colonies with morphological signs of erythroid differentiation had accumulated EpoR.

The blast cells in the colonies on the membranes (representing myeloid differentiation) have accumulated mostly at the stage of differentiation where they have already acquired the receptor for IL-3, but not for erythropoietin, GM-CSF or G-CSF, whereas the myeloperoxidase-positive colonies with morphological signs of myeloid differentiation had accumulated GM-CSF-R and G-CSF-R.

Stem Cells in the Bone Marrow

To study the maturation of hematopoietic cells in the bone marrow of the irradiated recipient mice, the animals were treated as described above and the BM cells from the femurs of syngeneic donors were injected intravenously ($10^5$ BM cells per mice) in the recipients. The animals received injections of NOS inhibitors (L-NAME, its inactive enantimere D-NAME and ETU) as described above, and mice were analyzed 7–10 days after transplantation.

The BM cells were tested for the presence of various growth factor receptors which serve as markers of the differentiation stage and indicate the presence of stem cells and multipotent precursor cells. The BM preparations were tested for cells expressing receptors to HSF (ligand of c-kit), GM-CSF, G-CSF and IL-3. The results Table 3 show that inhibition of NO synthesis in the recipient animals after BM transfer leads to dramatic increase in the number of c-kit-positive and IL-3-R-positive cells, suggesting that the population of cells in the BM becomes highly enriched in hematopoietic stem cells. At the same time the number of cells expressing receptors for G-CSF, which marks the later stages of differentiation, decreases almost three-fold, while the number of GM-CSF-R-positive cells is slightly decreased. This suggests that inhibition of NOS during hematopoiesis selectively enriches the BM in undifferentiated stem cells which have already acquired c-kit and IL3 receptors, but have not proceeded to the later stages when the receptor for G-CSF is synthesized.

TABLE 3

Presence of hematopoietic markers in BM cells of irradiated

| mice after injection of NOS inhibitors | | | | |
|---|---|---|---|---|
| Markers | c-kit | IL-3-R | G-CSF-R | GM-CSF-R |
| control (no injections) | 2% | 7% | 24% | 18% |
| treatment with L-NAME | 46% | 58% | 12% | 13% |
| treatment with ETU | 84% | 83% | 8% | 10% |
| treatment with D-NAME | 7% | 12% | 19% | 16% |

Reversibility of the NOS Inhibitors' Action in BM Cells

The critical question is whether undifferentiated stem cells which accumulate in the bone marrow as a result of treatment with NOS inhibitors have the capacity to revert to normal state and resume normal hematopoiesis process once the action of NOS inhibitors is suspended. The failure to do so might indicate that the cells become stranded in their undifferentiated status, similar to various pathological conditions. To answer this question, the treatment of mice with NOS inhibitors was halted 7–9 days after the BM transfer and checked the BM cells for the presence of hematopoiesis markers 1–7 days after termination of injections. Control mice continued to receive the daily injections. The results (Table 4) demonstrate that once the treatment with inhibitors of NOS is suspended, the cells were able to resume their differentiation and to proceed to the later stages normally. This indicates that enrichment in stem cells after treatment with NOS inhibitors is reversible and can be used to "boost" the number of stem cells before inducing them to proceed further along their differentiation pathways.

TABLE 4

Presence of hematopoietic markers in BM cells of irradiated mice after injection of NOS inhibitors and subsequent suspension of treatment

| Markers | c-kit | IL-3-R | G-CSF-R | GM-CSF-R |
|---|---|---|---|---|
| treatment with L-NAME for 8 days | 78% | 77% | 9% | 11% |
| treatment with L-NAME for 13 days | 82% | 84% | 9% | 12% |
| 1 day after suspension of treatment | 62% | 71% | 15% | 14% |
| 2 days after suspension of treatment | 29% | 37% | 16% | 14% |
| 3 days after suspension of treatment | 9% | 28% | 18% | 18% |
| 5 days after suspension of treatment | 8% | 14% | 28% | 21% |
| 7 days after suspension of treatment | 5% | 12% | 26% | 20% |

NOS Inhibition and Apoptosis

To test whether prolonged treatment with NOS inhibitors affects the rate of programmed cell death in BM cells, the number of apoptotic cells in the preparation of BM cells was examined. The TUNEL approach was used, thus revealing the cells with intensely fragmented DNA, a hallmark of apoptosis, at the same time using the DAPI staining to visualize the nuclei of all cells in the preparation. The results indicate that neither prolonged treatment with L-NAME, nor with ETU did not affect the proportion of apoptotic cells (8+/−3% in control versus 7+/− in L-NAME treated and 8%+/− in ETU-treated animals). Similarly, suspension of treatment with inhibitors did not affect programmed cell death in BM preparations (9+/−4% of TUNEL-positive cells). This suggests that manipulation of NOS activity in the animals after BMT, although having profound effect on differentiation and maturation of hematopoietic cells, does not affect the extent of programmed cell death in BM cells, further supporting the feasibility of applications of NOS inhibitors for therapy.

Example 3

Nitric Oxide Regulates Brain Development in Vertebrates

It has been recently demonstrated that nitric oxide (NO), a multifunctional second messenger, is involved in cell and tissue differentiation and organism development. NO synthase (NOS) controls the transition from cell proliferation to growth arrest and, as a result, regulates the balance between cell proliferation and differentiation in cultured neuronal cells, in developing Drosophila, and during hematopoiesis in mammals (Peunova et al., 1996; Kuzin et al., 1996; Michurina et al., 1997). Here, whether NOS is involved in the brain development in vertebrate animals was tested. Xenopus laevis was chosen as a model organism for these studies, focusing the investigation on the formation of the brain. The Xenopus NOS gene was cloned and the distribution of NOS-positive neurons in the developing brain was studied. It was found that inhibition of NOS dramatically increases the number of cells in the developing brain, and increases the overall size of the brain. The results suggest that NOS is directly involved in the control of cell proliferation and neuronal differentiation in the developing vertebrate brain.

Cloning of the Xenopus NOS Gene

Using the information about the known NOS genes, the NOS cDNA from Xenopus (XnNOS) was cloned. Analysis of its primary structure suggests that the cloned gene represents the homologue of the $Ca^{2+}$-dependent neuronal NOS isoform of mammals. Analysis of the gene reveals a remarkable degree of evolutionary conservation with long stretches of amino acid sequences identical to those of humans, mice, rats, and Drosophila. The cloned gene produces enzymatically active protein when transfected in cultured cells. The primary structure of the gene made it possible to obtain a specific antibody, and the immunofluorescence analysis indicates that the diaphorase staining of the developing Xenopus correctly represents the distribution of the XnNOS enzyme. This notion is supported by in situ hybridization analysis of XnNOS transcripts in the tadpole brain. The cloned gene is now being used to isolate other putative NOS genes from Xenopus.

NOS is Expressed in a Consistent Spatio-Temporal Pattern in the Developing Xenopus Brain The Xenopus brain undergoes histogenesis starting at stage 39–40; prior to that, the neural tube consists of rapidly dividing undifferentiated neuroepithelial cells. In the growing brain of the Xenopus tadpole, new cells arise in the narrow zone of the germinal layer in a defined pattern, which can be revealed by labeling with BrdU. The distribution of NADPH-diaphorase staining (which is indicative of NOS expression) in Xenopus brain from stage 40 through stage 50 was analyzed. Zones of staining first appeared at stage 43, the time of migration of young neurons off the neural tube and their differentiation. Staining appeared outside of the germinal layer and became more intense as development of tadpoles proceeded. The most intense staining was observed in single large differentiated neurons in the tectum and spinal cord, and in the marginal zone of the tectum composed of processes of differentiated neurons. The gradient of diaphorase staining was latero-medial and reciprocal to the pattern of proliferation, suggesting that zones of active proliferation in the germinal layer remained free of NOS activity through these stages.

Inhibition of NOS in the Developing Brain Resulted in Excessive Proliferation of Young Neurons To test whether NOS is involved in growth arrest in neuronal precursors in the developing Xenopus brain, NO production was blocked by introducing pieces of plastic impregnated with NOS inhibitors, L-NAME and ETU, into the ventricle of the tadpole's brain at stage 43. After 3, 7 and 12 days, animals were examined for changes in the patterns of cell division, differentiation, survival, and morphology of the brain. BrdU labeling demonstrated a dramatic increase in the number of cells in the S phase of the cell cycle in the inhibitor treated brains, compared to the control brains. The number of BrdU-positive cells in the tectum consistently increased throughout the experiment. Staining of cell nuclei with DAPI revealed higher number of cells in the brain sections in each time interval of the experiment, indicating that excessive cells in the S phase successfully completed the cell cycle by mitosis.

Inhibition of NOS and Programmed Cell Death

Whether the inhibition of NOS and excessive proliferation of cells in the developing brain affects the programmed death of neurons in the tectum was tested. Using the TUNEL technique to visualize the apoptotic cells in the brain, it was found that at day 3 the number of TUNEL-positive cells was the same in both the control and inhibitor treated tectum. However, after 7 and 12 days, there were more apoptotic cells in the brains of animals which received NOS inhibitors, than in control animals. The increase in the number of TUNEL-positive cells is not due to toxicity of the inhibitors, since cells continued to incorporate BrdU very effectively. Identical changes were observed with two structurally unrelated inhibitors of NOS, indicating that the effects resulted specifically from blocking NOS activity. This data suggests that excessive proliferation of cells in the tectum leads to activation of programmed death acting to remove the surplus neurons. Alternatively, this may indicate that differentiated neurons became dependent on NO for survival, similar to the situation in fully differentiated PC12 cells (Peunova et al., 1996).

Neuronal Differentiation in the Brain is Affected By Inhibition of NOS

To test whether excessive cell proliferation induced by NOS inhibitors affects the distribution and differentiation of neurons in the Xenopus brain, antibodies to specific neuronal markers which have a specific and highly reproducible pattern of expression during Xenopus development were used. It was found that the distribution of neurons positive for Islet-1, N-tubulin, and N CAM was changed after inhibition of NOS. In particular, the neurons were displaced into the marginal zone, neurons in the intermediate layer were more heterogeneous and with shorter branches than in control brains, and the distinct layered structure of the tectum was altered. In addition, the number of Islet-1 positive motor neurons was increased after inhibition of NOS.

Inhibition of NOS Leads to Ectopic Proliferation of Neuronal Precursors

The Xenopus brain has a fine cytoarchitecture. Groups of neighboring cells share the place and time of birth and become involved in common local circuits. The position of young and mature neurons in the brain is strictly dependent on the place of their birth, migration, and final differentiation, and compose a characteristic pattern. In the brains of animals treated with inhibitors of NOS, it was found, in addition to extra layers of young dividing neuronal precursors, numerous ectopic sites of neuronal proliferation. Large clusters of cells were observed in atypical location, occupying the marginal zone, various areas of the tectum, the telencephalon and the hindbrain.

Inhibition of NOS Increases the Overall Size of the Brain

Inhibition of NOS activity in the brains of developing tadpoles resulted in increased number of cells in the S-phase, accompanied by a modest increase in programmed cell death at late stages. Together, this increased the total number of cells in the brain and consequently increased the overall size of the brain. The most affected areas are the optic tectum and the area immediately adjacent to the ventricle where the impregnated piece of plastic was inserted. In cases when the source of the NOS inhibitor was shifted in the ventricle towards the telencephalon or hindbrain regions in the developing brain, an increase in size of the anterior the posterior parts of the brain, respectively was observed.

Taken together, these results demonstrate that No controls the number of neurons in the developing brain, and inhibition of NOS directly affects the size of the Xenopus brain. This confirms the role of NO as a general regulator of cell and tissue differentiation in the organism. This suggests that manipulations of the NO levels may be used for therapeutic purposes to control proliferation and subsequent differentiation of nerve cells in replacement therapy after neurodegenerative disorders caused by aging (e.g., Alzheimers, Parkinson's or Huntington's), stroke, or trauma.

Equivalents

While this invention has been particularly shown and described with reference to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of increasing a population of precursor cells in a tissue of a mammal, comprising contacting said tissue with an inhibitor of nitric oxide, thereby increasing the population of precursor cells in the tissue.

2. The method according to claim 1, wherein the precursor cells are osteoblasts, chondrocytes, mesenchymal stem cells, keratinocytes, or neural precursors.

3. The method according to claim 1, wherein the tissue is skin, bone, digestive epithelium, fat tissue, bone marrow stroma, cartilage, tendon, muscle, brain, pancreas, reproductive organs or neural tissue.

4. The method according to claim 3, wherein the tissue is skin, muscle, brain, pancreas, reproductive organs or neural tissue.

5. The method according to claim 1, wherein the inhibitor of nitric oxide is an inhibitor of nitric oxide synthase.

6. A method of regenerating tissue in an adult mammal, comprising contacting the tissue with an inhibitor of nitric oxide.

7. The method according to claim 6, wherein the tissue is skin, muscle, bone, digestive epithelium, fat tissue, bone marrow stroma, cartilage, neural tissue or tendon.

8. The method according to claim 6, wherein the inhibitor is an inhibitor of nitric oxide synthase.

9. The method according to claim 6, which results in an increase in the size of the tissue.

10. A method of obtaining a population of precursor cells, comprising contacting a precursor cell with an inhibitor of nitric oxide, thereby obtaining a population of precursor cells.

11. The method according to claim 10, further comprising isolating the population of precursor cells from non-precursor cells.

* * * * *